(12) United States Patent
Malchau et al.

(10) Patent No.: US 9,554,731 B2
(45) Date of Patent: Jan. 31, 2017

(54) PATIENT POSITIONING SYSTEMS AND METHODS

(75) Inventors: Henrik Malchau, Boston, MA (US); Gavin Braithwaite, Cambridge, MA (US); Orhun K Muratoglu, Cambridge, MA (US); Harry E. Rubash, Weston, MA (US); Bayen Lee Miller, Medford, MA (US)

(73) Assignee: The General Hospital Corporation, Boston, MA (US)

( * ) Notice: Subject to any disclaimer, the term of this patent is extended or adjusted under 35 U.S.C. 154(b) by 553 days.

(21) Appl. No.: 13/369,036

(22) Filed: Feb. 8, 2012

(65) Prior Publication Data

US 2012/0203140 A1    Aug. 9, 2012

Related U.S. Application Data

(60) Provisional application No. 61/440,446, filed on Feb. 8, 2011, provisional application No. 61/508,851, filed on Jul. 18, 2011.

(51) Int. Cl.
| | |
|---|---|
| *A61B 5/103* | (2006.01) |
| *A61B 5/117* | (2016.01) |
| *A61B 17/58* | (2006.01) |
| *A61B 17/60* | (2006.01) |
| *A61F 2/00* | (2006.01) |

(Continued)

(52) U.S. Cl.
CPC .............. *A61B 5/1114* (2013.01); *A61B 34/20* (2016.02); *A61B 5/1127* (2013.01); *A61B 5/4571* (2013.01); *A61B 5/6823* (2013.01); *A61B 5/6878* (2013.01); *A61B 5/70* (2013.01); *A61B 2034/2048* (2016.02); *A61B 2505/05* (2013.01)

(58) Field of Classification Search
CPC ....... A61B 2560/00; A61B 5/00; G06F 159/00
USPC ........... 600/407, 587, 595; 606/88, 102, 130
See application file for complete search history.

(56) References Cited

U.S. PATENT DOCUMENTS

| | | | | |
|---|---|---|---|---|
| 6,524,260 | B2 * | 2/2003 | Shechtman et al. | 600/594 |
| 7,291,118 | B2 * | 11/2007 | McFarland et al. | 600/587 |
| 7,996,061 | B2 * | 8/2011 | Mollard et al. | 600/424 |

(Continued)

FOREIGN PATENT DOCUMENTS

| | | |
|---|---|---|
| WO | 2009117832 A1 | 10/2009 |
| WO | 2010111224 A1 | 9/2010 |

OTHER PUBLICATIONS

"9 Degrees of Freedom—Razor IMU—AHRS compatible." Sparkfun Electronics Product Description. Accessed Jan. 17, 2012. http://www.sparkfun.com/products/9623.

(Continued)

*Primary Examiner* — Rene Towa
*Assistant Examiner* — May Abouelela
(74) *Attorney, Agent, or Firm* — Quarles & Brady LLP

(57) ABSTRACT

Systems and methods provide patient position information to a user. A patient positioning device is placed on a patient in a predefined location. The patient positioning device determines a relative patient position with respect to at least one known reference axis. The patient positioning device communicates patient position information including or with reference to the at least one known reference axis. The communicated patient position information allows the user to position the patient and/or a surgical tool using the communicated patient position information.

17 Claims, 14 Drawing Sheets

(51) Int. Cl.
*A61B 5/11* (2006.01)
*A61B 5/00* (2006.01)

(56) References Cited

U.S. PATENT DOCUMENTS

| | | | |
|---|---|---|---|
| 8,167,823 B2* | 5/2012 | Nycz et al. | 600/587 |
| 8,271,066 B2* | 9/2012 | Sarin et al. | 600/407 |
| 8,308,663 B2* | 11/2012 | Tuma et al. | 600/595 |
| 8,337,426 B2* | 12/2012 | Nycz | 600/587 |
| 8,675,939 B2* | 3/2014 | Moctezuma de la Barrera | 382/131 |
| 8,790,351 B2* | 7/2014 | Paradis et al. | 606/91 |
| 2001/0044578 A1* | 11/2001 | Ben-Haim et al. | 600/424 |
| 2003/0153829 A1* | 8/2003 | Sarin et al. | 600/426 |
| 2004/0097952 A1* | 5/2004 | Sarin et al. | 606/102 |
| 2004/0101104 A1* | 5/2004 | Avinash | A61B 6/032 378/98.12 |
| 2004/0254584 A1* | 12/2004 | Sarin et al. | 606/102 |
| 2004/0254586 A1* | 12/2004 | Sarin et al. | 606/130 |
| 2005/0065617 A1* | 3/2005 | Moctezuma de la Barrera et al. | 623/908 |
| 2006/0095047 A1* | 5/2006 | de la Barrera | 606/102 |
| 2006/0122541 A1* | 6/2006 | Tuma | 600/587 |
| 2007/0106282 A1* | 5/2007 | Lavallee | 606/1 |
| 2007/0112286 A1 | 5/2007 | Prichard | |
| 2007/0118056 A1* | 5/2007 | Wang et al. | 600/595 |
| 2007/0249967 A1* | 10/2007 | Buly et al. | 600/595 |
| 2007/0265526 A1 | 11/2007 | Govari et al. | |
| 2008/0172055 A1* | 7/2008 | Mollard et al. | 606/87 |
| 2008/0214932 A1* | 9/2008 | Mollard et al. | 600/429 |
| 2008/0249394 A1* | 10/2008 | Giori et al. | 600/407 |
| 2009/0105714 A1* | 4/2009 | Kozak | 606/102 |
| 2009/0306679 A1* | 12/2009 | Murphy | 606/130 |
| 2010/0137869 A1* | 6/2010 | Borja et al. | 606/88 |
| 2010/0137871 A1* | 6/2010 | Borja | 606/91 |
| 2010/0324457 A1 | 12/2010 | Bean et al. | |
| 2011/0060220 A1 | 3/2011 | Roche et al. | |
| 2011/0154569 A1* | 6/2011 | Wiggers | A61B 6/0407 5/81.1 R |
| 2012/0016269 A1* | 1/2012 | Moctezuma de la Barrera | 600/595 |
| 2012/0116412 A1* | 5/2012 | Penenberg | 606/102 |
| 2012/0157887 A1* | 6/2012 | Fanson et al. | 600/595 |

OTHER PUBLICATIONS

PCT International Preliminary Report on Patentability for PCT/US2012/024339.
European Patent Office, Extended European Search Report, Application No. 12744158.2, Dec. 15, 2014, 16 pages.
Japan Patent Office, Notification of Reasons for Refusal, Application No. 2013-553525, Nov. 24, 2015, 5 pages.

* cited by examiner

PATIENT POSITIONING SYSTEMS AND METHODS

CROSS-REFERENCE TO RELATED APPLICATIONS

This application claims the benefit of U.S. Provisional Patent Application Ser. No. 61/440,446, filed Feb. 8, 2011, and entitled "Patient Positioning Device," which is hereby incorporated by reference.

This application also claims the benefit of U.S. Provisional Patent Application Ser. No. 61/508,851, filed Jul. 18, 2011, and entitled "Patient Positioning Systems and Methods," which is hereby incorporated by reference.

STATEMENT REGARDING FEDERALLY SPONSORED RESEARCH OR DEVELOPMENT

Not applicable.

BACKGROUND OF THE INVENTION

The subject matter disclosed herein relates generally to positioning systems and methods, and, more particularly, to patient positioning systems and methods that provide patient positioning information relative to one or more predetermined references.

In many, if not all patient related procedures, the patient and/or surgical instruments are positioned in such a way as to provide the best surgical access and outcomes, while minimizing potential risk to the patient. Most patient positions include some degree of risk, and this risk can be amplified in an anaesthetized patient who cannot make others aware of conditions related to their position. In addition, because many patients are transferred and positioned on operating tables in preparation for a variety of surgical procedures, the desired patient position must be reassessed after repositioning.

Because there is a need for accurate patient positioning information, there are systems that are currently available for aiding in patient and/or surgical instrument positioning. These systems require and/or incorporate a dedicated surgical room with dedicated positioning related equipment, which all requires a high upfront cost. These dedicated room systems generally assist a user with determining where in the dedicated room a surgical instrument or patient landmark is located relative to a known fixed point or points in the room, and often require extensive training, dedicated computers, are expensive, and are typically bulky (a whole room), to track a spatial location and/or movement of a surgical instrument or landmark in or on the patient. They frequently require implanted landmarks to operate accurately.

In a variety of orthopedic implant procedures, such as total hip replacement (THR) or arthroplasty, total knee arthroplasty (TKA), high tibial osteotomy (HTO), and total shoulder replacement (TSR), for example, the optimal orientation of the surgical implant can enhance initial function and long term operability of the implant. When dedicated positioning systems are not used, simple "eyeballing" methods or mechanical tools may be used. For example, eyeballing has been used for the alignment of a prosthetic acetabular cup or femoral broach. It has been found that eyeballing is not sufficiently accurate to reliably align and place implant components with the bones to which such components are attached.

One recent study reported on the postoperative complication risk for a THR. One factor identified was the orientation of the acetabular prosthetic cup. The report concluded that malpositioning of the acetabular cup can be linked to many unfavorable clinical outcomes, including increased rate of dislocation of the hip joint, acetabular liner fracture, increased wear, decreased joint motion, joint pain, and hastened failure of the implant. Thus, studies have demonstrated that malpositioning or sub-optimally-positioned orthopedic implants correlates to improper loading, increased implant wear, and even implant failure.

Therefore, correct positioning of the patient before and during a surgical procedure so as to accurately use surgical instruments and place implants, as used in a surgical procedure with respect to the patient's anatomy, is an important factor in achieving a successful outcome.

It would, therefore, be desirable to provide systems and methods that use a small, self-contained device to provide patient specific position information relative to a predetermined reference before and/or during surgical procedures.

BRIEF DESCRIPTION OF THE INVENTION

The present invention overcomes the aforementioned drawbacks by providing systems and methods that provide patient position information to a user. In particular, a self-contained patient positioning device capable of being placed on a patient is configured to determine and communicate patient position information, including the at least one known reference axis. The communicated patient position information allows the user to position the patient and/or a surgical tool using the communicated patient position information without simple "eyeballing" estimations or extensive, whole-room-integrated positioning systems.

In accordance with one embodiment of the invention, a method is provided for providing patient position information. The method comprises placing a patient positioning device on a patient in a predefined location. The patient positioning device is calibrated to determine at least one known reference axis. The patient positioning device communicates patient position information to a user, the patient position information including the at least one known reference axis. The communicated patient position information allows the user to position the patient and/or a surgical tool using the communicated patient position information.

The patient positioning device may be calibrated to map an x-axis, a y-axis, and a z-axis to an orientation relative to gravity. The patient positioning device may also measure rotational acceleration around any of the x-axis, the y-axis, and the z-axis and can use other reference planes as well, such as magnetic fields or direction of wireless base-stations.

In accordance with another embodiment of the invention, a method is provided for positioning a patient and/or a surgical tool during a total hip replacement procedure. The method comprises placing a patient positioning device on a patient in a predefined location. The patient positioning device is calibrated to determine a horizontal reference of a pelvis of the patient while the patient is standing. The patient is then placed in a lateral position. The patient positioning device relates the horizontal reference of the pelvis to a gravitational reference, and communicates patient position information to a user. The patient position information includes an angular displacement between the horizontal reference of the pelvis and the gravitational reference. The position of the pelvis can be verified using the communicated patient position information, and the pelvis and/or the surgical tool can be repositioned based on the communicated patient position information.

In accordance with another embodiment of the invention, a system is provided for providing patient position information. The system comprises a patient positioning device that is configured to be removably secured to a patient in a predefined location, the patient positioning device including a position sensing system and a communication system. The position sensing system is configured to determine at least one known reference axis. The communication system is configured to communicate patient position information to a display, the patient position information including the at least one known reference axis. The display displays the patient position information for use by a user to allow the user to position the patient with reference to the at least one known reference axis.

BRIEF DESCRIPTION OF THE DRAWINGS

The present invention will become more apparent from the detailed description set forth below when taken in conjunction with the drawings, in which like elements bear like reference numerals.

DETAILED DESCRIPTION OF THE INVENTION

Figure 1:
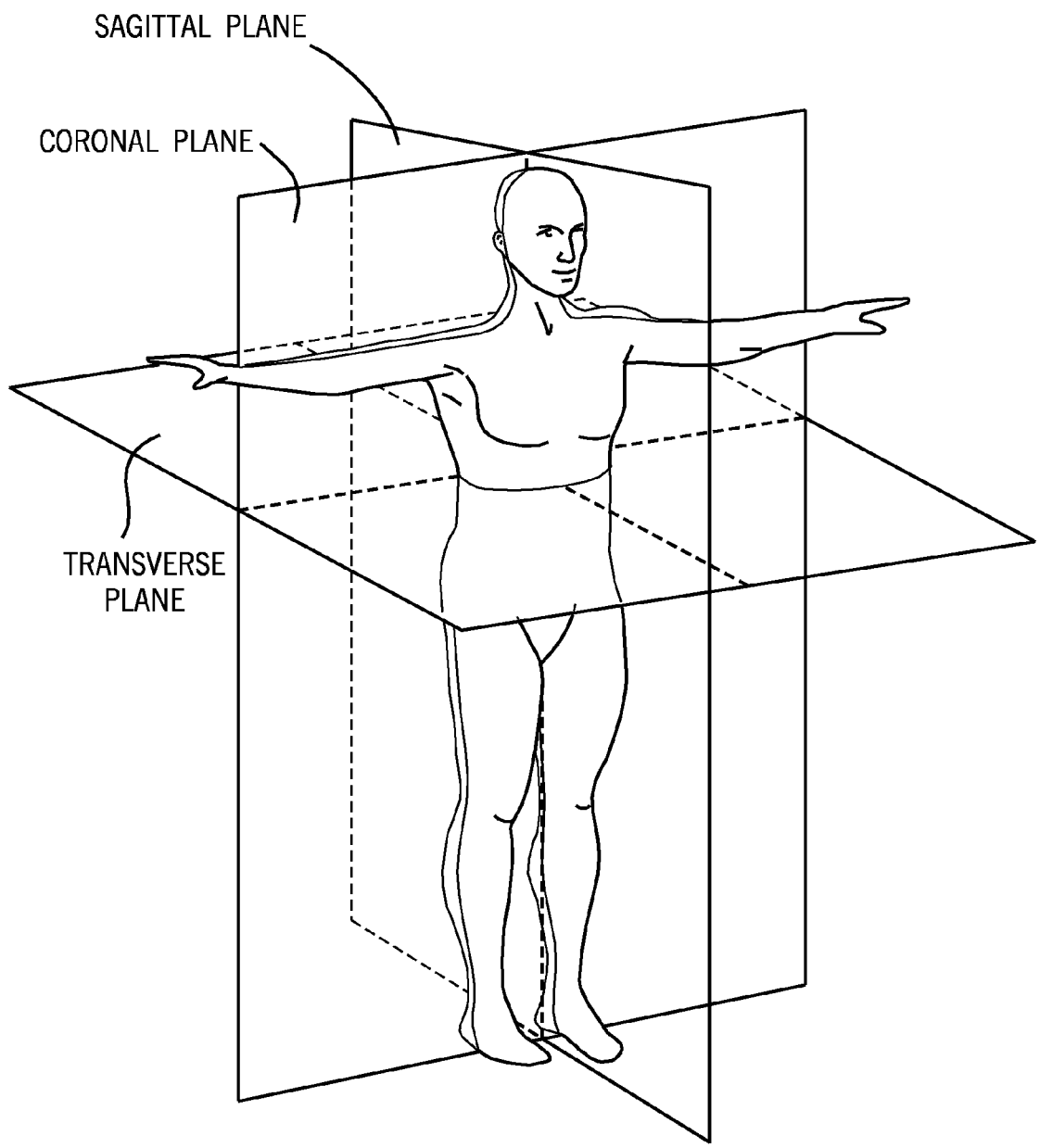
FIG. 1 is a view showing the three planes typically used to describe the planes of the human body.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures depict selected embodiments and are not intended to limit the scope of embodiments of the invention. Skilled artisans will recognize the examples provided herein have many useful alternatives and fall within the scope of embodiments of the invention.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically, such as when elements or features are embodied in program code. Thus, although the figures depict example arrangements of processing elements, additional intervening elements, devices, features, components, or code may be present in an actual embodiment.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, diodes, look-up tables, etc., which may carry out a variety of functions under the control of one or more microprocessors or other control devices. Other embodiments may employ program code, or code in combination with other circuit components.

In accordance with the practices of persons skilled in the art of computer programming, the present disclosure may be described herein with reference to symbolic representations of operations that may be performed by various computing components, modules, or devices. Such operations may be referred to as being computer-executed, computerized, software-implemented, or computer-implemented. It will be appreciated that operations that can be symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

The various aspects of the invention will be described in connection with positioning a patient for and/or during a total hip replacement (THR) procedure. That is because the features and advantages that arise due to the invention are well suited to this purpose. However, it should be appreciated that the invention is applicable to other procedures and to achieve other objectives as well.

Figure 2:
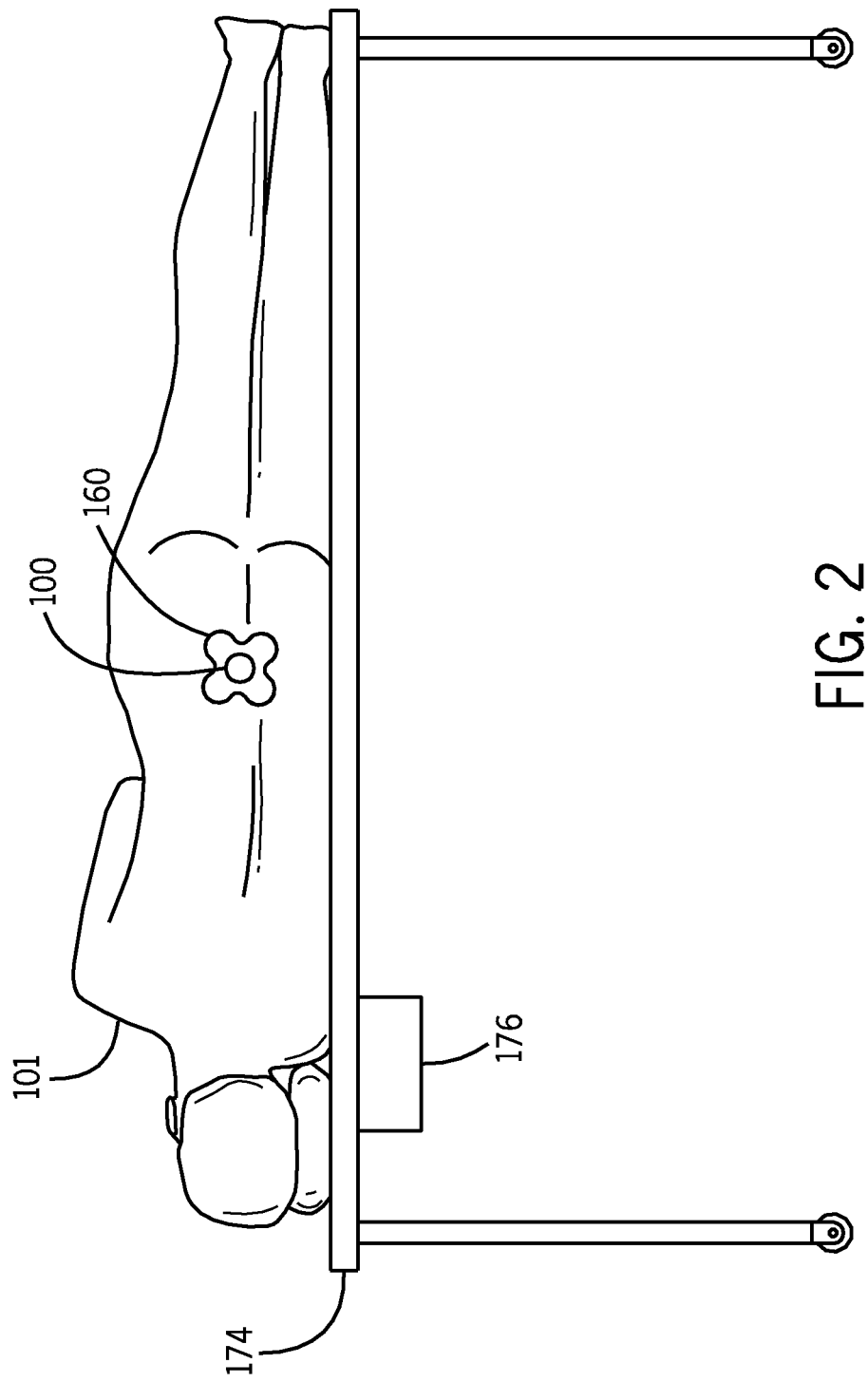
FIG. 2 is a view showing a patient lying in a left lateral decubitus portion on an operating table.

In clinical settings, certain terms are used with general consistency. For example, a variety of common patient orientations are described using common, clinical phrases and terms. As a specific example, patient planes may include a coronal plane, transverse plane and sagittal plane. Referring to FIG. 1, the coronal plane (sometimes referred to as the frontal plane) may be defined as the plane parallel to the chest of the patient and divides the body into ventral and dorsal (belly and back) sections. Likewise, the transverse plane may be defined as the plane that divides the body into superior and inferior parts. Furthermore, the sagittal plane may be a vertical plane which passes from front to rear dividing the body into right and left sections. In addition, referring to FIG. 2, the lateral decubitus position may refer to the patient being oriented, usually prone, on the operating table with one hip aligned above the other. By way of example with reference to FIG. 2, if the patient is lying on the left side, this is termed the "left lateral decubitus."

Figure 3:
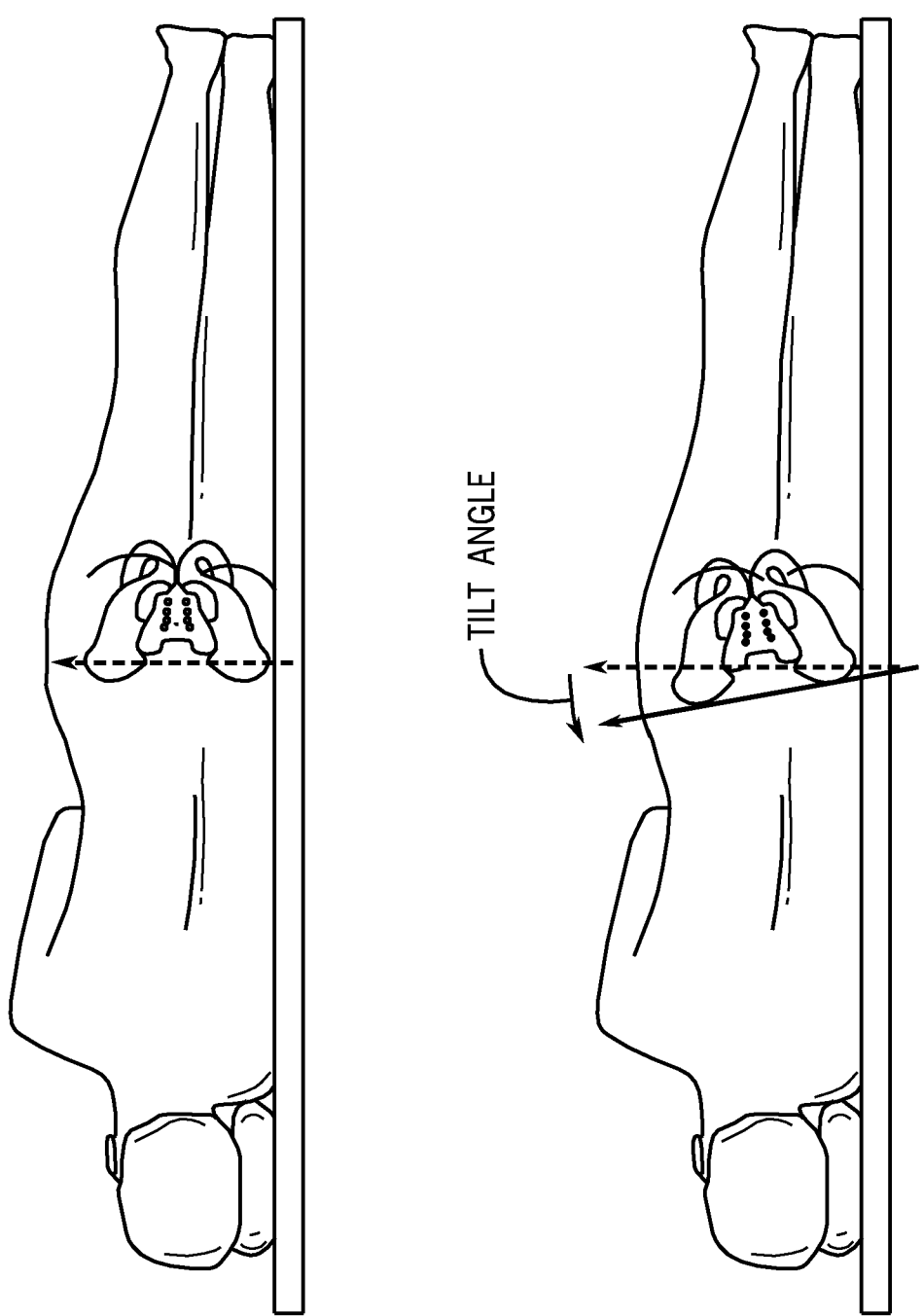
FIG. 3 is a view showing an example of positive coronal tilt of a patient in a left lateral decubitus position, with the vertical plane of the pelvis marked with a dashed line and the tilt angle identified.
Figure 4:
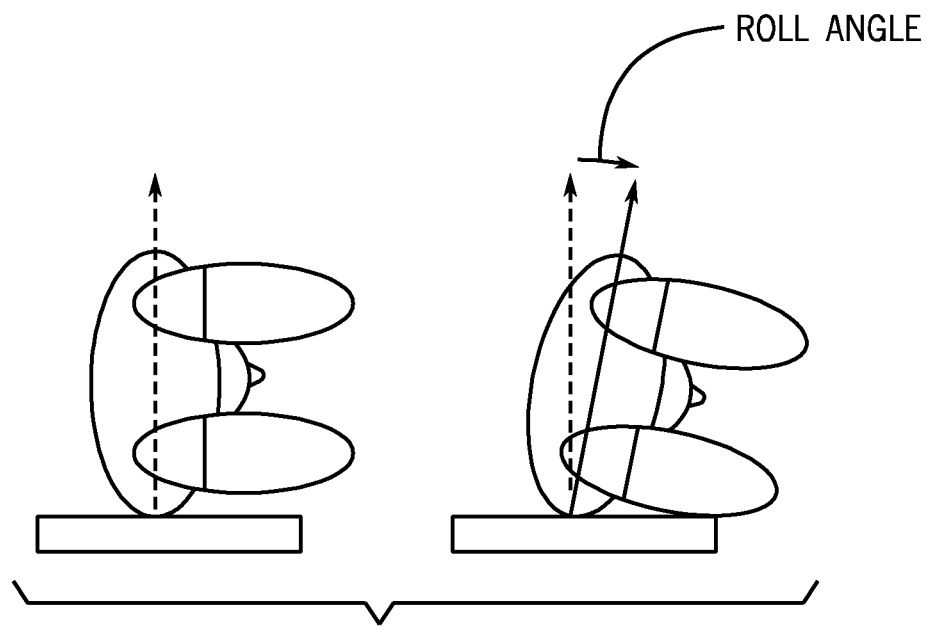
FIG. 4 is a view showing an example of forward roll, with the axis of the patient marked with a dashed line and the roll angle identified.

Building upon the above terms and referring to FIG. 3, a coronal tilt may refer to the rotation of the pelvis within the coronal plane. Physically, one hip rotates towards the head, and one towards the toes, such as illustrated in FIG. 3. Accordingly, a positive coronal tilt may be defined as the rotation of the pelvis such that the upper hip moves towards the head. Likewise, a Left lateral decubitus positive coronal tilt defines an orientation where the patient is lying on their left side and the right hip has rotated towards the head.

Figure 5:
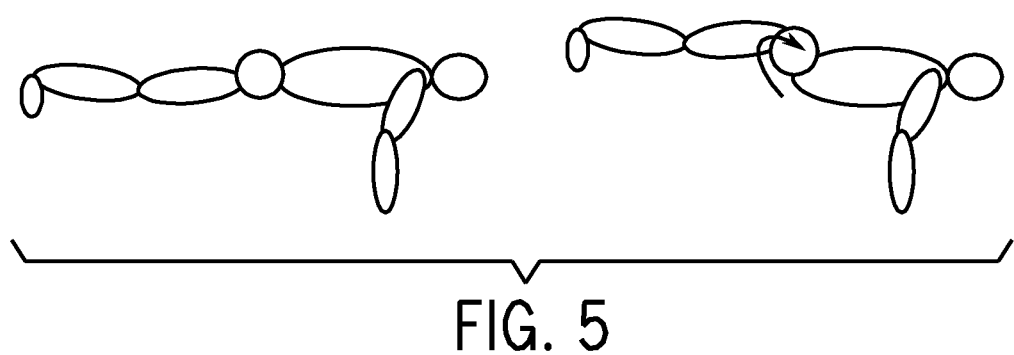
FIG. 5 is a view showing an example of negative rotation where the pelvis is tucked up towards the spine.

Further still and referring to FIG. 5, roll may refer to the rotation of the patient around the central (long) axis (within the transverse plane, around the normal to transverse plane). Physically, it is the rolling of the patient out of vertical towards a table. As such, positive forward roll may refer to the patient rolling face-forwards towards a table. Rotation may refer to as the rotation of the patient around the posterior superior iliac spine (PSIS). Physically, it is the rotation of the pelvis in towards in the coronal plane of the patient. Negative rotation may be defined as "tucking the rear up toward the spine."

Figure 6:
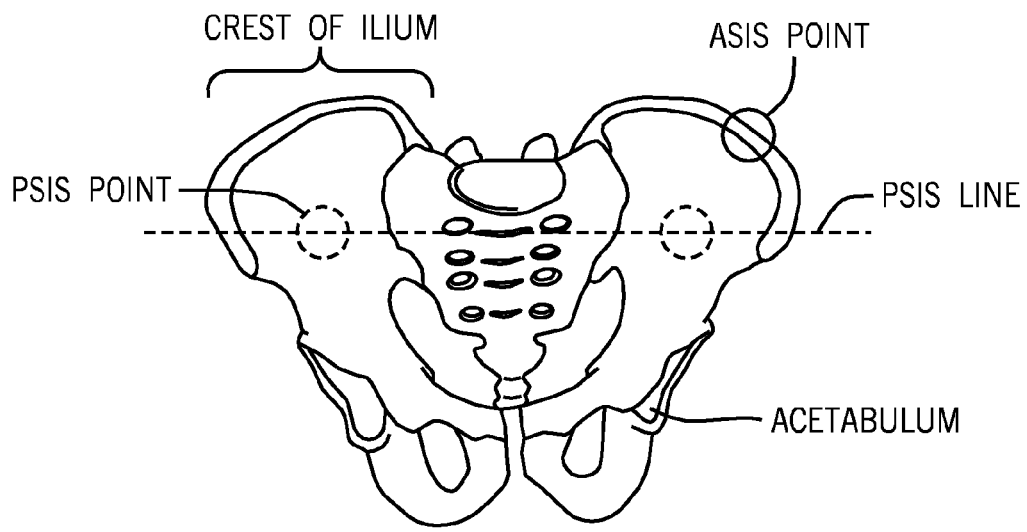
FIG. 6 is an anatomical view showing pelvic structure, including the ASIS and PSIS.

Thus, posterior superior iliac spine (PSIS) may refer to a projection at the posterior end of the iliac crest. Referring to FIG. 6, the left and right PSIS defines a line that is used in hip surgery and is expected to be collinear with a known vertical line in the operating room. As a corollary, anterior superior iliac spine (ASIS) defines a landmark of surface anatomy, and refers to the anterior extremity of the iliac crest of the pelvis.

As previously discussed, systems are available that provide patient positioning information, but the known systems are not standalone systems or units, and instead often require a dedicated room and merely provide a reference between two or more related fixed units in the room. The present invention overcomes many of these limits, for example, by providing a device including at least a sensor that is capable of discerning relative position information based on a reference that does not require systems, such as room-integrated reference systems, to discern the relative position information. For example, the sensor may be configured to utilize a reference axis, such as provided by gravity. A problem with this configuration is that gravity can only provide position information relative to an x-axis and a y-axis, but cannot provide position information relative the gravitational axis, or z-axis. The orientation around the x-axis and the y-axis are known, where they compose the "floor" plane, or horizontal, but the rotation around the z-axis, the axis aligned with gravity, or vertical, is not known. However, such limitations may be suitable in some clinical applications.

In some configurations, position sensing equipment may use inertial systems, such as gyroscopes, and relative accelerations, which allows motion in all directions to be tracked. However, the signal processing required in such systems can be involved and, in some clinical applications, prohibitive. Furthermore, commercially available systems including such inertial- and acceleration-based sensing devices require "zeroing" and "re-zeroing" because the internal sensors only have limited sensitivity. As a result, in such an implementation using a gyroscope, resolving the orientation around all axes may be limited within a few degrees. Additional gyroscopes can be used to reduce such limitations but at an additional cost of material and complexity.

The practical solution is to find a way to provide a second, orthogonal reference axis for a patient positioning device. Since low cost accelerometers are available and do not require external references other than gravity, they can be a desirable choice for many clinical applications. By addition of acceleration in a known direction, the final "lost" direction (rotation around the z-axis) can be obtained.

Figure 7:
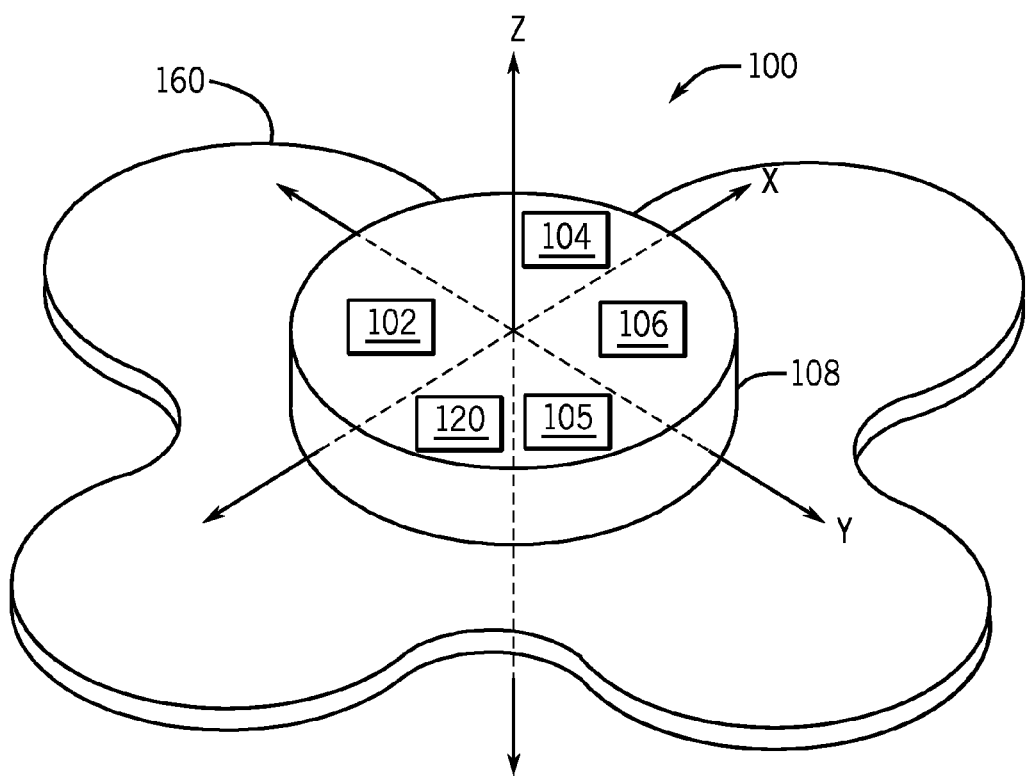
FIG. 7 is a view of a patient positioning system in accordance with the present embodiments.

Referring now to the drawings wherein like reference numbers correspond to similar components throughout the several views and, specifically, referring to FIG. 7, embodiments of the invention shall be described in the context of a patient positioning device (PPD) 100. The PPD is configured to operate with systems and be usable within methods configured to provide patient specific position information, including but not limited to measurements of inclination and tilt, and in some embodiments, rotation.

Embodiments of the PPD 100 described herein can include a position sensing system 102, a processing system 104 and a communication system 106. Embodiments of each system are described below. For power requirements, the PPD 100 may be powered with a rechargeable or primary battery 120, or the PPD 100 may be plugged in to an appropriate wall outlet (not shown) for power or another power supply.

In some embodiments, the position sensing system 102 can include one or more accelerometers, gyroscopes, or triangulation systems based on external references. One example of a system using a triangulation system based on external references is a camera, such as implemented in the some commercially available video game systems, such as produced by Nintendo of America of Redmond, Wash., under the Wii trademark.

In some embodiments, the position sensing system 102 can be internally referenced in a self-contained housing 108, such as that shown in FIG. 7. In this configuration, there may be no other external hardware telling the PPD 100 where it is in relation to a reference. With such a self-contained unit that has no external references, other than gravity, it may not be possible to know absolutely the orientation of the unit within a space.

In some embodiments, the position sensing system 102 may include additional sensors capable of determining absolute orientation of the PPD relative to a known reference, usually the direction of gravity. The PPD 100 may also include other sensors to allow absolute determination of position and orientation through the use of either rotational accelerometers, or triangulation sensors, for example.

Figure 18:
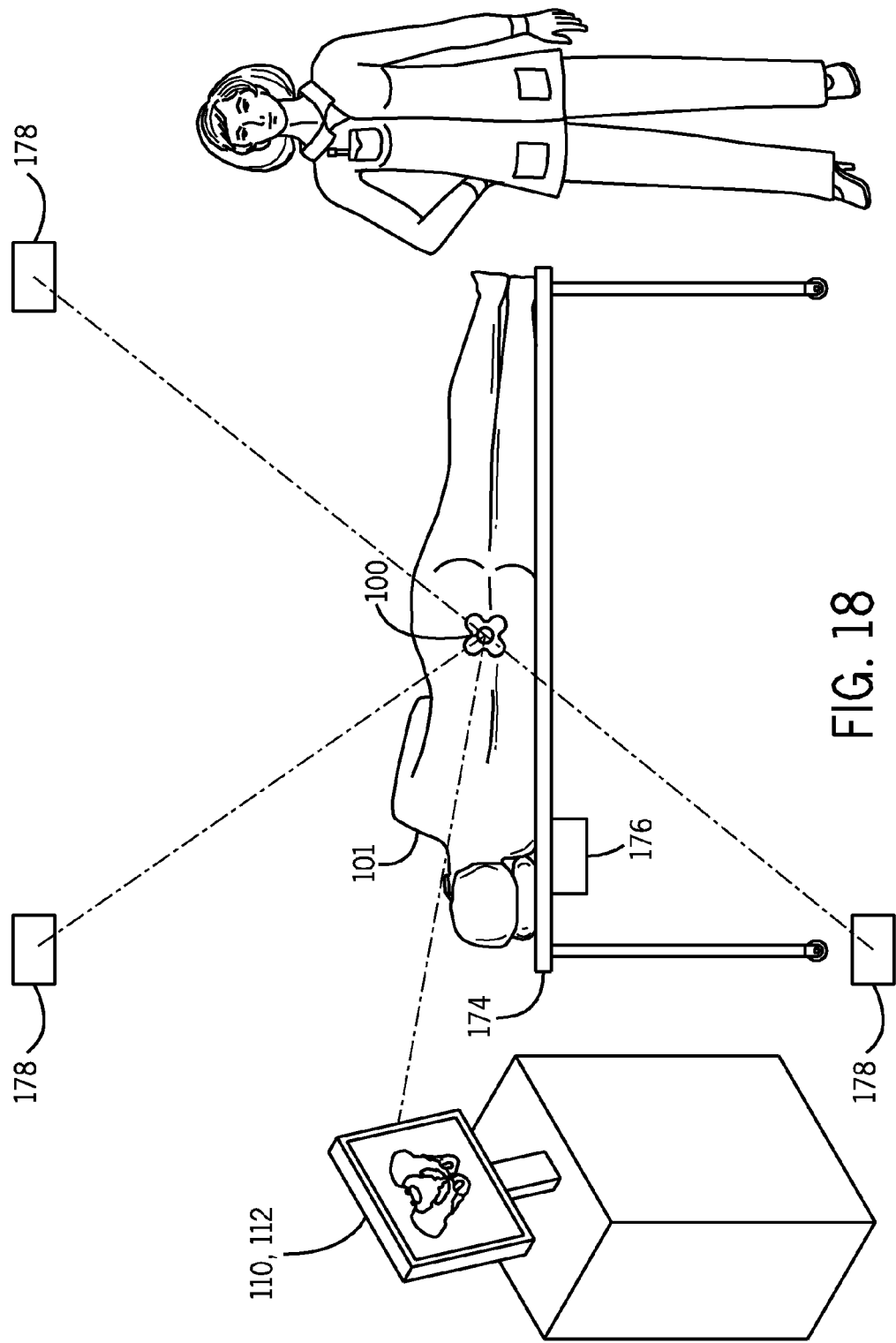
FIG. 18 is a view showing a patient positioning device using external radio sources to triangulate position.

Some embodiments allow the calibration of the PPD 100 without any additional devices. For example, referring to FIGS. 2, 7, and 18, in order to impart some motion, the surgeon may gently rock the patient 101. If the y-axis is aligned exactly perpendicular to the direction of rocking, no acceleration will be observed in this channel, and acceleration will be seen in the x-axis. Any slight rotation of the sensor will result in more acceleration being picked up in the y-axis channel. In an additional option, the surgeon deliberately tilts the operating table 174 (more easily done with modern motorized beds) so that a second reference direction can be introduced and the unknown rotation is resolved.

In other embodiments, the PPD 100 may be calibrated with the aid of additional devices. For example, the table 174 that supports the patient 101 may be instrumented to allow the direction of the PPD 100 to be referenced against the plane or orientation of the bed.

For example, a lateral acceleration may be imparted to the patient by an impulse device 176 mounted to the table 174, or to the patient, or to the PPD 100, to provide a pulsatile motion in one direction only that can be used to differentiate true special orientation around the gravity vector. In this configuration, the concept relies on the extra acceleration induced by the impulse device 176 being rigidly orientated relative to gravity. When ready, the surgeon may trigger the impulse device 176 to drive a gentle acceleration in line with where the x-axis should be. Any extra signal in the y-axis indicates a rotation.

In one embodiment the position sensing system 102 of the PPD 100 may include a three axis accelerometer. The PPD 100 may be referenced in a horizontal position as the patient is standing, and then the patient lies down, at which point the PPD 100 is vertical. Referencing against gravity, the PPD 100 can detect tilt and roll, but may not be capable of detecting rotation because this motion is around the gravity direction. However, as previously described, if the clinician gently pushes the patient in the roll direction, or nudges the table 174 in the roll direction, the resultant acceleration allows the rotation of the PPD 100, and hence that of patient's pelvis, to be determined. In this configuration, all critical motions and locations of the patient's pelvis can be determined.

Alternative scenarios for determining this unknown rotation axis may include the use of a gyroscope (as above); LED illumination and tracking using a camera; an arm that locks to a reference point on the table, yielding an external reference angle; and/or triangulation with surrounding sensors, as non-limiting examples.

In other embodiments, the exact, or near exact rotation of the PPD 100 in all three dimensions may be determined using an external reference for determining rotation in the gravitational axis. This external reference may be an orientationally invariant target visible to the PPD 100 on the table 174 or in the operating room.

It is noted that the use of a gyroscope may be limited where the data is streamed continuously because constant telemetry is required to know motion at any particular time using such an inertial-based system. One solution to this is generally constant communication with the processor unit 110. Alternatively, the processing can be performed in the processing system 104 on-board the PPD 100 itself, and the data may only be transmitted when the information is requested. This approach saves battery power and minimizes the possibility of interference with operating room systems.

Generally, it is often preferable for the PPD 100 therefore to track and store continuously in memory 105 its three dimensional orientation and rotation providing that information to the processor 110 or the display 112 wirelessly when requested. Such three dimensional orientation and rotation information or positional information may be stored and/or communicated using, for example, concepts of pitch, yaw, and roll, such as defined in aviation and with respect to coronal, transverse, and sagittal planes.

In yet an additional embodiment, the direction of a Bluetooth or Wi-Fi signal, for example, may be used to provide a new reference axis. In use, when it is known where the signal is coming from, a new reference axis can be provided based on the fixed direction of the signal to obtain all three rotation axis. Signal strength, triangulation, or Time Difference of Arrival (TDOA) may all be used to provide this information.

Similarly, external radio sources, such as Bluetooth receivers 178, may be used by the PPD 100 to triangulate position. For example, radio sources could be placed in three corners of the operating room. The radio sources would not need to be calibrated, because it's the changes in position that provides relevant data. In its simplest configuration, the receiver radio for the PPD 100 could be placed at a known location on the operating table. For example, the receiver radio for the PPD 100 could be placed at one end of the table on the center of the edge. In this example, the direction of the radio source provides adequate information to fully resolve rotation of the pelvis around the gravitational axis.

In an additional embodiment, a magnetometer may be used to provide reference to the earth's magnetic field. An example of such a magnetometer chip is the Honeywell HMC5843. There may be equipment in the operating room that might produce some interference for the magnetometer, but in use that doesn't matter so long as the interfering equipment is stationary, and most large ferromagnetic sources or electrical interferences should be stationary. It is also possible to provide a secondary electromagnetic reference pole by the use of an oscillating magnetic field, as would be generated by an electromagnetic coil, or through a static magnet. These reference poles could be pointed on the surgical table, or they may be external to the surgical area.

In a further embodiment, the rotation about the gravitation axis may be obtained by movement of the patient, or titling of the table 174 such that the gravitational vector is no longer parallel to an axis of the sensor. Because the tilt of the table is defined relative to the patient, this information allows absolute determination of all relevant orientations of the pelvis.

In an alternative embodiment, more than one PPD, or remote sensors coupled to the PPD 100, may be used to spread the footprint of the PPD to reduce possible effects of skin motion. It is possible that tension on the skin may move the PPD 100. By putting on more than one PPD 100, or remote sensors coupled to the PPD 100, in different locations, skin motion may be able to be calculated out versus bulk motion of the patient's position. For example, two or more adhesive pads may be placed a predetermined distance apart from each other that would be well clear of any skin motion. The intervening area needn't be adhered. This configuration will also allow critical surgical sites to remain clear, such as spinal access during spinal anesthesia. In a similar configuration, a remote sensor(s), may be on a pad sized less than about one cm square (for example, a suitable accelerometer, the ADXL335, is only about 4×4×1.45 mm, and a suitable magnetometer, the HMC 5883L, is only about 3×3×0.9 mm) that could then have power and data connection to a separate adhesive pad remote from the surgical area. This configuration reduces the footprint of the device in the critical area, e.g., at the base of the spine, and therefore eases comfort and increases accuracy.

Figure 19C:
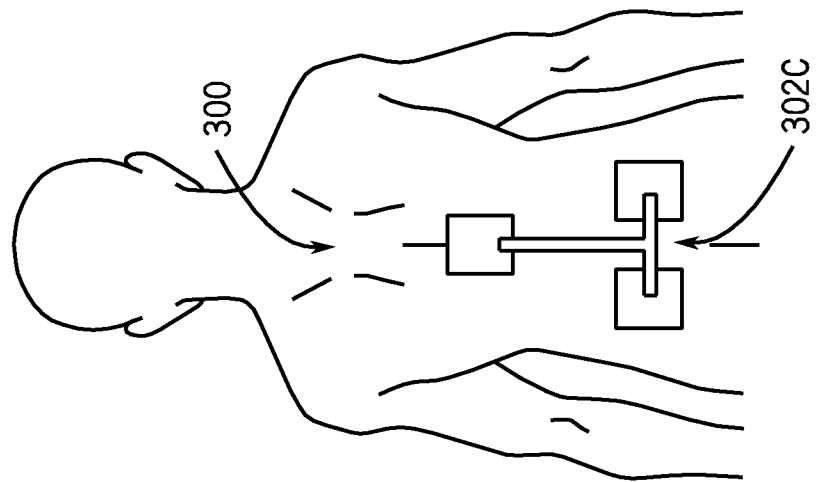
FIGS. 19A-C are rear elevational views of a patient's back having a spine position monitoring system mounted thereon.
Figure 19B:
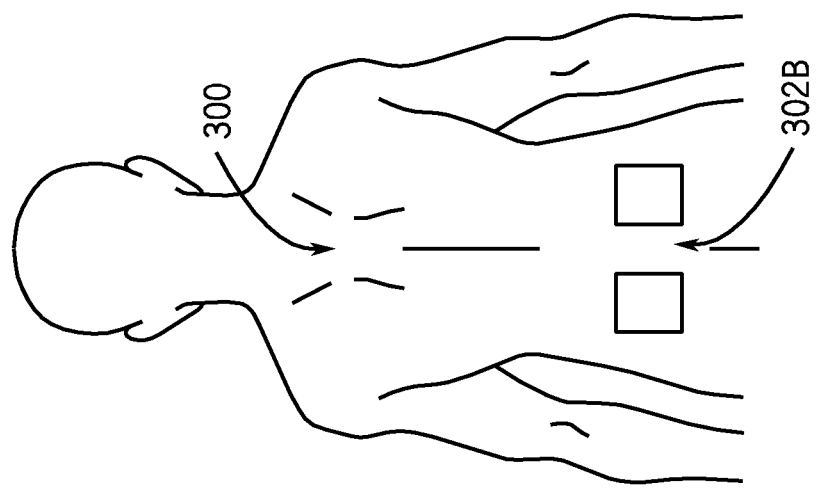
Figure 19A:
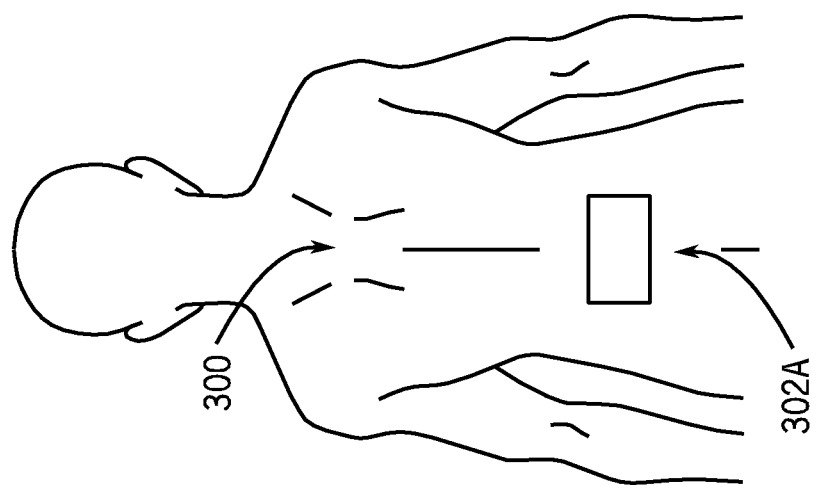
Figure 20:
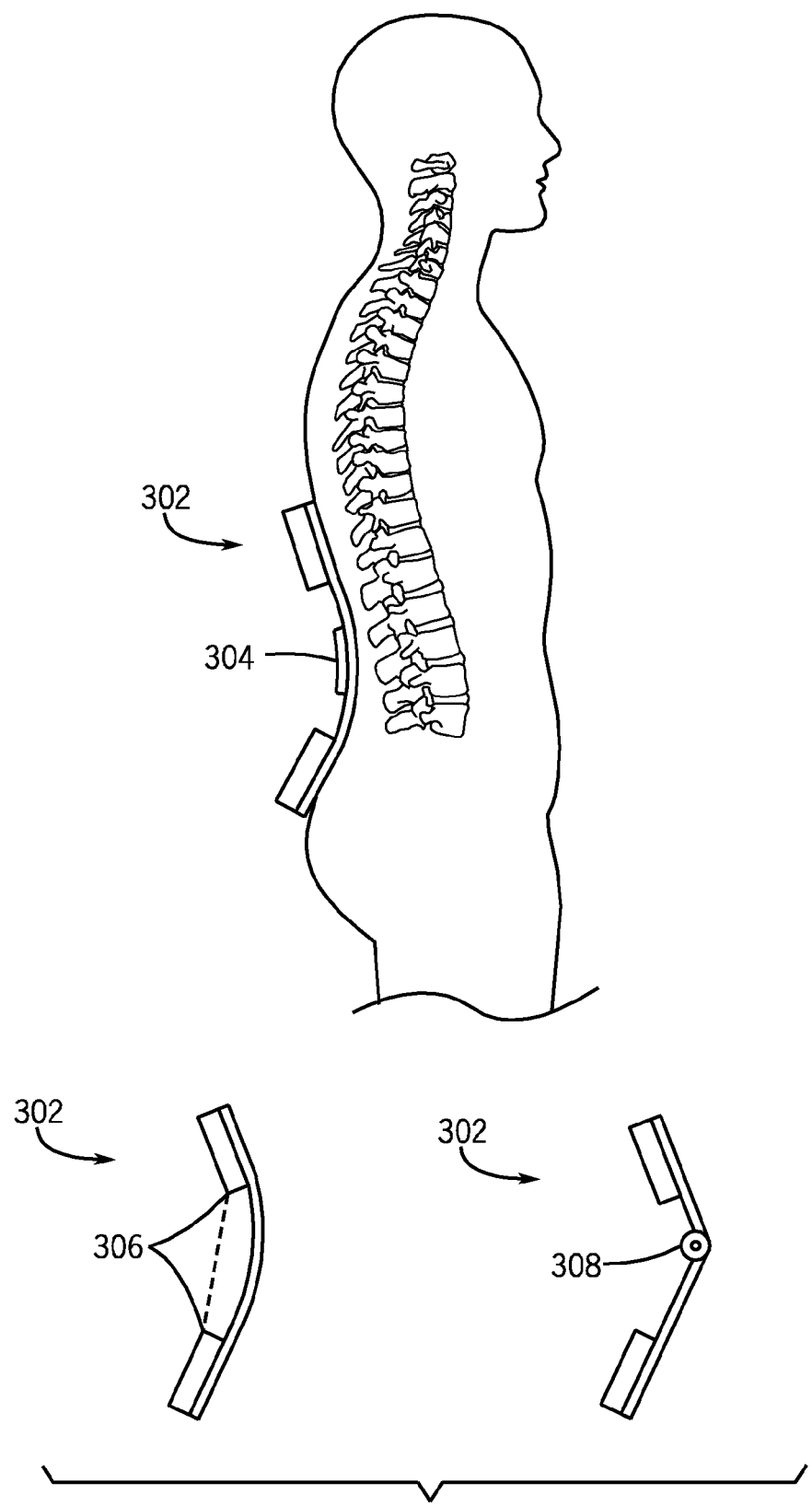
FIG. 20 is a schematic illustration of a variety of configurations for the spine position monitoring system of FIGS. 19A-C.

Referring to FIGS. 19A-C and 20, in another alternative embodiment, the spine 300 may be monitored and used to provide data relative to a tuck position. For example, a monitoring system 302A, 302B, 302C that may employ a flexible sheet may be mounted in a predefined location on or near the spine, (e.g., below L4) and the other end may be mounted somewhere near L1 or L2, as illustrated in FIGS. 19A-C, or could also be adhered in the middle of the spine 300. As further illustrated in FIGS. 19A-C, the monitoring system may take a variety of configurations, including, for example, localized pads 302A, opposing pads 302B, and combinations thereof 302C and may be oriented vertically, horizontally, at angles there between, or along multiple axes. Regardless of the specific mounting position or configuration of the monitoring system 302A, 302B, and 302C, there is some element of bend due to the natural orientation of the spine 300, such as illustrated in the detailed plan views of the monitoring systems 302 illustrated in FIG. 20. However an appreciable amount of bend would come from spine 300 being oriented in the tuck position described above. The monitoring system 302 may incorporate a variety of instruments to measure and provide tuck related data including strain gauges 304, length sensors 306, or even a hinge with an angle measure 308. A measure of distance moved may be sufficient to provide useful position information.

Figure 8:
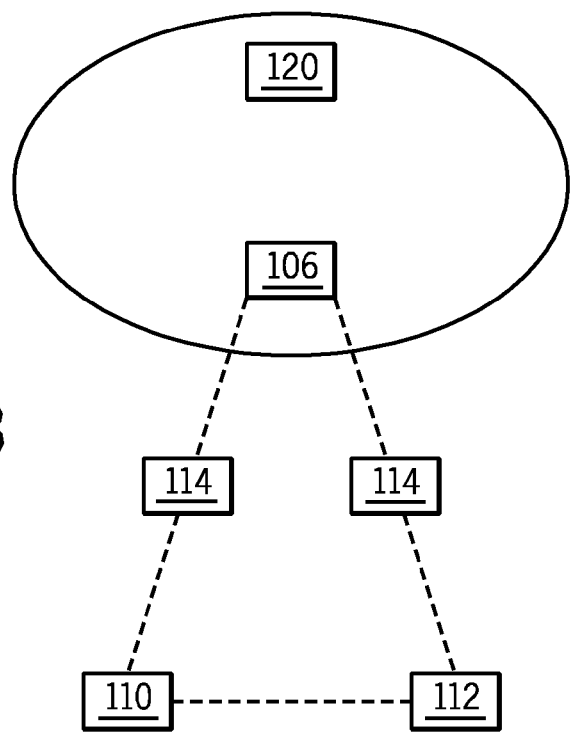
FIG. 8 is a view showing an embodiment of a communication system as part of the patient positioning device shown in FIG. 7.

Referring now to FIG. 8, the communications system 106 may be Bluetooth, wireless, or wired, as non-limiting examples, and may be configured to communicate with a processor unit 110 and/or a suitable display 112. It is to be appreciated that any known or future developed communication system is contemplated for use with the PPD 100. The processor unit 110 may be a laptop or a simple human interface device such as a touch screen or smart phone (e.g., iPhone or iPad type devices). In some embodiments, the communications system 106 may communicate with a communications receiver 114 that is coupled or connected to the processor unit 110 and/or the display 112, for example.

The processor 110 and/or the display 112 may display PPD data including raw and/or manipulated orientation information, and/or position information relative to a starting or reference position. In use, the processor 110, and/or the display 112 or other appropriate devices, provides information, such as position and/or orientation information, to a user, such as a surgeon. The position information, for example, may take on a variety of forms. For example, the position information may be in the form of a go or no-go indication, such as a green indication for when the patient, or an implant, or a tool is within acceptable user defined limits, such as an acceptable angle range for the procedure, or a red indication for when the patient, implant, or tool is outside the acceptable angle range for the procedure. The position information may also be in the form of angular data feedback. The angular data could be used by the surgeon to determine when the patient, implant, or tool is within or outside the acceptable angle range for the procedure.

Figure 9:
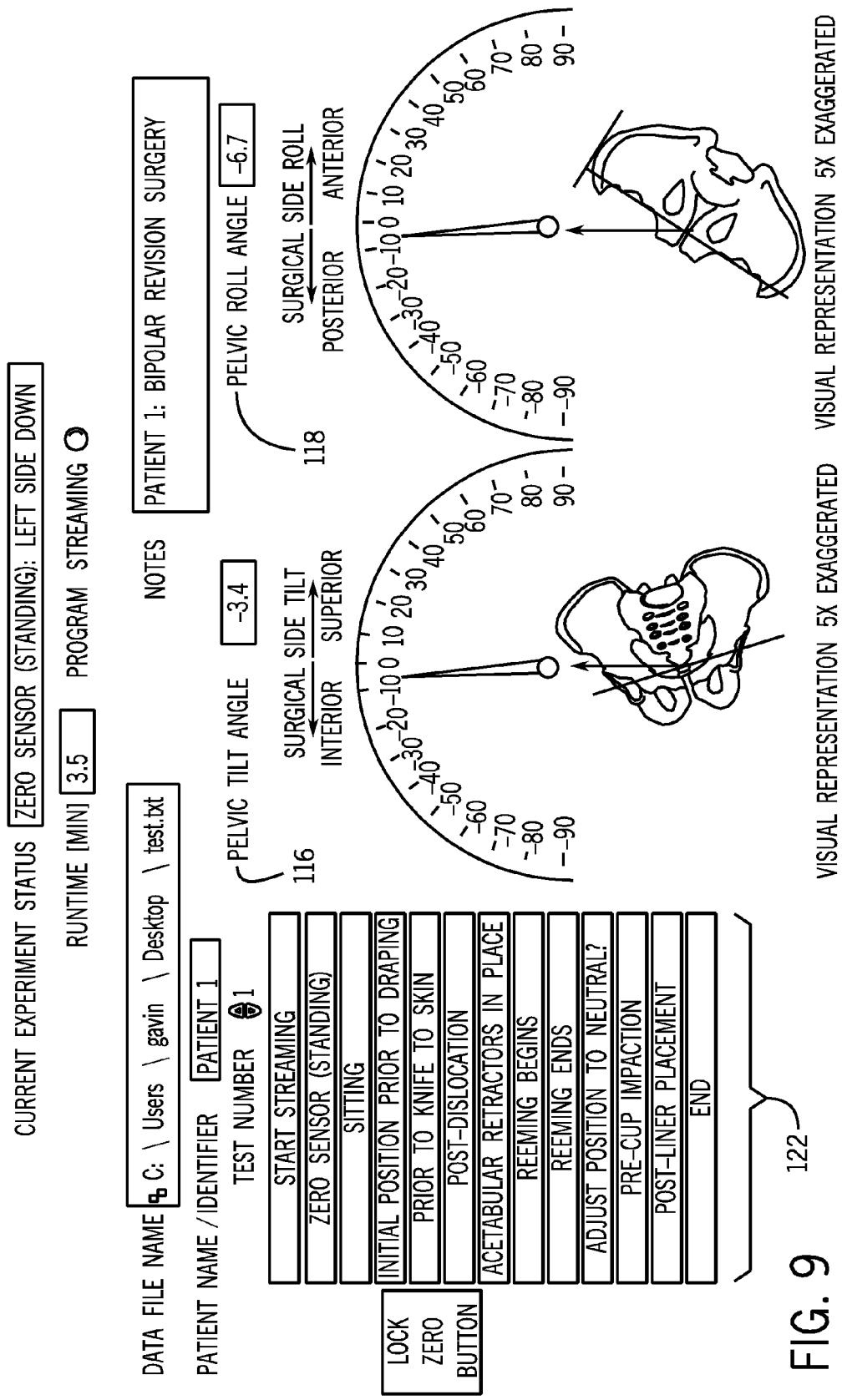
FIG. 9 is a graphical representation of positional information displayable on a display or other device.

Graphical feedback may also be provided to the surgeon. For example, a graphical representation of the hip and associated anatomical features may be displayed on the display 112 with positional information identified to guide the surgeon for placement of the implant within the acceptable angle range for the procedure. An example of a graphical feedback is provided in FIG. 9. As can be seen, a pelvic tilt angle 116 and a pelvic roll angle 118 may be provided in one or both numerical form and graphical form, as non-limiting examples. User interface controls may also be incorporated into the display 112 (or processing unit 110). The user interface portion 122 may include selections for activities during the procedure, and may alter the graphical feedback provided depending on the current activity.

It is to be appreciated that any of these forms of position information may be combined or presented individually, and may include audible indications as well. It is to be appreciated that the PPD data may be presented in any or a variety of spatial relationships.

The processing system 104 may include one or more processors 107 and memory 105, and may be configured to be responsible for control of the PPD 100. The processing system 104 may also be configured to manage communications via the communication system 106.

Since, unlike traditional, room-integrated systems, the PPD 100 is small and compact, and does not require an integral display, although embodiments may include a display, it can be packaged in a variety of shapes beneficial for the particular application. As non-limiting examples, size and shape may range from a pack of cards to a wrist watch, similar to the shape shown in FIG. 7, or to a bandage, or larger or smaller. Packaging and mounting options are therefore very flexible but may be designed to mount the PPD 100 in a predetermined location on the patient to aid in ready positional detection. In some embodiments, the PPD 100 may be secured relative to the ASIS or PSIS line (see FIG. 2) or its vicinity by the use of a belt, glue, tape, compression bandage, transcutaneous osseous pins, etc., as non-limiting examples. In some embodiments, the PPD 100 is secured with a tape or bandage with enough openings to allow for the application of spinal anesthesia to the patient without removing the tape or the bandage that holds the PPD 100. In some embodiments, the tape or bandage will have cutouts to enable the application of spinal anesthesia. In some embodiments, the tape or bandage holding the PPD 100 will be sutured the patient's skin.

Figure 10:
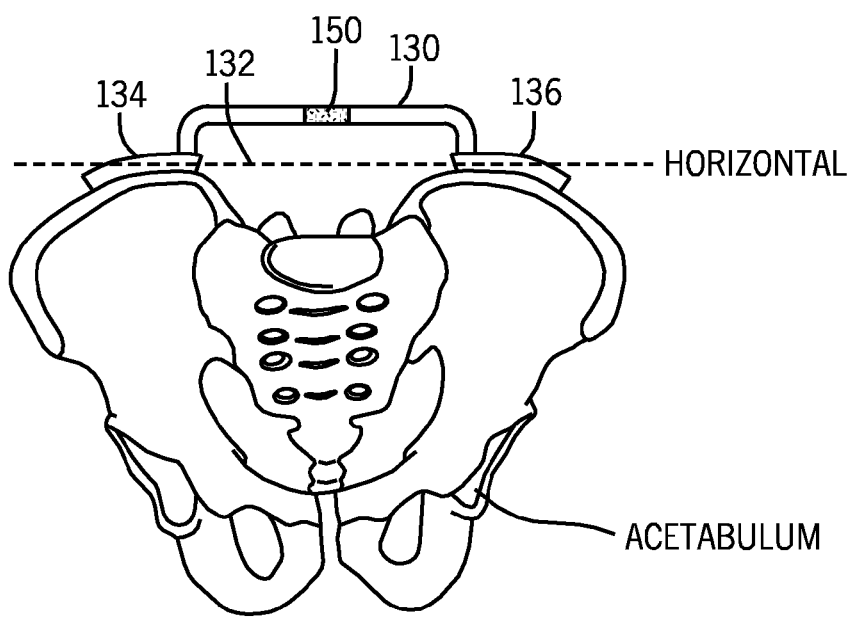
FIG. 10 is an anatomical view of the pelvic region with a brace configured to aid in defining the horizontal and to support a patient positioning device.

In some embodiments, a pelvic brace 130 may be used to define the horizontal line when the patient is standing (see FIG. 10). The PPD 100 may or may not be attached to the patient or the brace 130 at this point. The brace 130 conforms equally on both sides to the ilium crest, or any other suitable mounting points. In some embodiments, the brace 130 can be a single piece and can wrap around the patient's back, or in other embodiments it can be two or more pieces. The horizontal line 132 is defined by the line that crosses the body center of the members 134, 136 of the brace that conforms to either side of the ilium crest.

Figure 11:
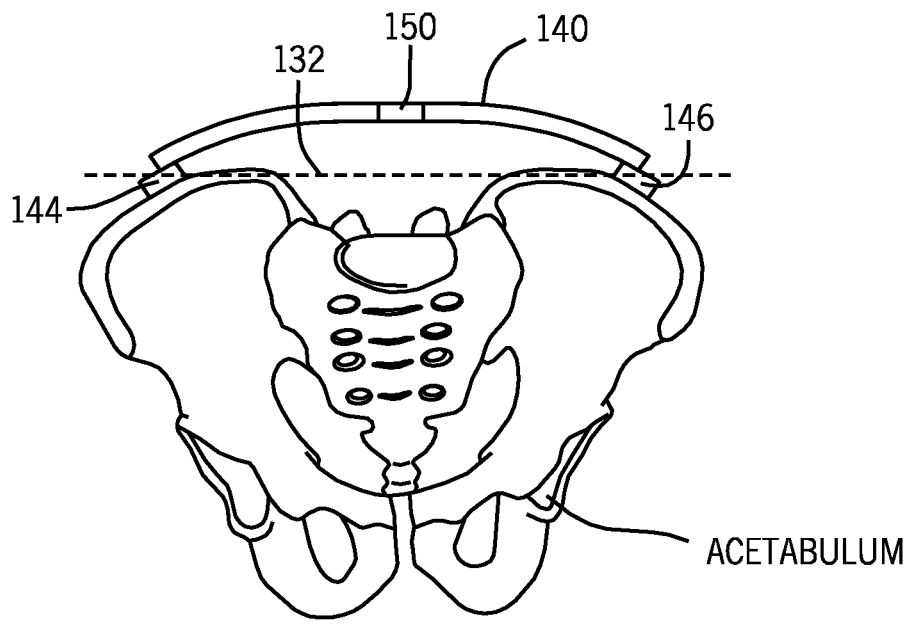
FIG. 11 is an anatomical view of the pelvic region with an alternative embodiment of the brace shown in FIG. 10.

Referring to FIG. 11, in an alternative embodiment, a pelvic brace 140 may conform to the ASIS. The body centers of the conforming members 144, 146 of the brace 140 may be used to define the horizontal line 132 when the patient is standing.

In some embodiments, a pelvic brace 130, 140 may be used to define the horizontal plane when the patient is lying supine (see FIG. 10). In this embodiment, the horizontal plane of the pelvic brace may be used to "zero" the horizontal plane of the PPD 100. Thus, lengthy monitoring of the patient during pre-op may be avoided and greater patient comfort may be achieved. In this embodiment, the PPD 100 may be placed on the patient's low back near the sacrum when the patient is in the supine position. In one embodiment, the ASIS points are palpated, and a brace with the conforming members may be placed on the ASIS points on the front of the patient. A second PPD 100 may be placed on the brace. The angle between the first PPD 100 that is on the lower back of the patient and the second PPD 100 that is on the brace may be recorded. The brace may then be removed after this referencing step and the surgery may proceed. This angle may be used to reference the first PPD 100 to the line that crosses the two ASIS points. Then, later in surgery, when the surgeon is ready to impact the acetabular cup into the pelvis, the first PPD 100 may be used to guide the insertion rod in at the proper angle. Typically, the angle between the line that crosses the ASIS points and the insertion rod is in a range of between about 20 degrees and about 70 degrees, more preferably between about 30 degrees and about 50 degrees, and more preferably between about 30 degrees and about 45 degrees, and most preferably between about 30 degrees and about 40 degrees. The second PPD 100 may also be mounted directly on the insertion rod.

In other embodiments, the patient may already be lying in the lateral decubitus position with the PPD 100 attached. A pelvic brace containing a second PPD 100 applied to the front of the pelvis, or on the ASIS points, or any other suitable mounting points, would allow reference of the vertical directly in the lying patient.

In some embodiments, either brace 130, 140 may contain a mounting system mechanism for retaining or supporting a PPD 100. For example, the brace may include slot 150 where the PPD 100 may be inserted and used to track changes in orientation of the patient position, such as during surgery, for example. The portion of the brace 130, 140 that includes the PPD slot 150 can remain attached to the patient during surgery, or in an alternative embodiment, the brace 130, 140 may be used to identify the horizontal, and then the brace may be removed and a second PPD 100 can be attached to the patient to reference the horizontal.

In some embodiments, the PPD 100 will be surgically secured the patient's pelvis.

In some embodiments, the PPD 100 will communicate with another sensor on a surgical tool, for instance an acetabular shell impactor. The surgeon holding the impactor will rotate the impactor until the target angle between the PPD 100 and impactor is achieved. This can be done by displaying the angle or the angles on a display 112 in the operating room. This can also be done by having circuit boards in either or both the PPD 100 and the impactor sensors displaying the angle(s) or displaying different color lights to indicate that the two devices (PPD 100 and impactor) are within the target range of angle(s).

Additional embodiments are contemplated for determining the leg length discrepancy and also for their correction. In some embodiments, separation of the femur from the pelvis could be determined optically, or through a transmitter/receiver pair, for example. In some embodiments, the PPD 100 may be placed on the low back of the patient either before any anesthesia and/or medication while the patient is standing, or while the patient is supine, as discussed above.

In one embodiment, the patient is asked to stand up to assess the difference in the length of the two limbs or the legs using blocks. Blocks of different heights may be placed below the foot of the shorter of the two legs until the pelvis is level, which may be measured by having the line that crosses the ASIS points level with the horizontal. Once the line that crosses the ASIS points is level with the horizontal, the total height of the blocks used may be measured to quantify the leg length difference that needs to be corrected during the subsequent total hip surgery.

In another embodiment, if the leg length discrepancy is primarily emanating from the discrepancy in the length of the femur, sensors may be placed on or around both knees to determine the distance between the PPD 100 at the low back of the patient and these sensors. The difference between the distances measured from the PPD 100 and the two sensors may be used as the leg length difference that needs to be corrected during the subsequent total hip surgery.

In another embodiment, if the patient has scoliosis, the leg length may be corrected if the spine is supple and not fixed.

In yet another embodiment, a reference bar (similar in nature to a pelvic brace) that spans the ankles or the bottom of the feet, for example, at the heel pad, may be used as a reference. In this embodiment, the reference bar contains two or more sensors to determine the distance between the PPD 100 at the low back of the patient and the reference bar. The sensors on the reference bar are placed such that one can geometrically determine the difference in the leg length of the patient. This reference bar can be permanently placed before draping the patient or can be applied intermittently during surgery as needed.

In yet additional embodiments, it is contemplated to use the PPD 100 in more complex configurations allowing access to different surgically relevant information. Additional sensors could be added to, for example, the femur to ensure that the critical axis of the femur is perpendicular with the critical axis of the pelvis. In addition, a sensor could be used to verify during the trial period that the leg length correction has been accurately applied. The sensor could be attached to the femur by adhesion, strapping, or bone screws, for example, or could be temporarily placed on reference points, such as small bone screws applied during surgery. A sensor could also be used to ensure that the femur, and hence the leg, has not been accidentally rotated during surgery.

Various methods of use of the PPD 100 will now be described in relation to, for only exemplary purposes, a THR. As previously described, this is because the PPD works well for this use. It is to be appreciated that other uses for positioning and orientation are contemplated as well. The steps performed while practicing a preferred embodiment of the invention are set forth in FIG. 12.

Figure 12:
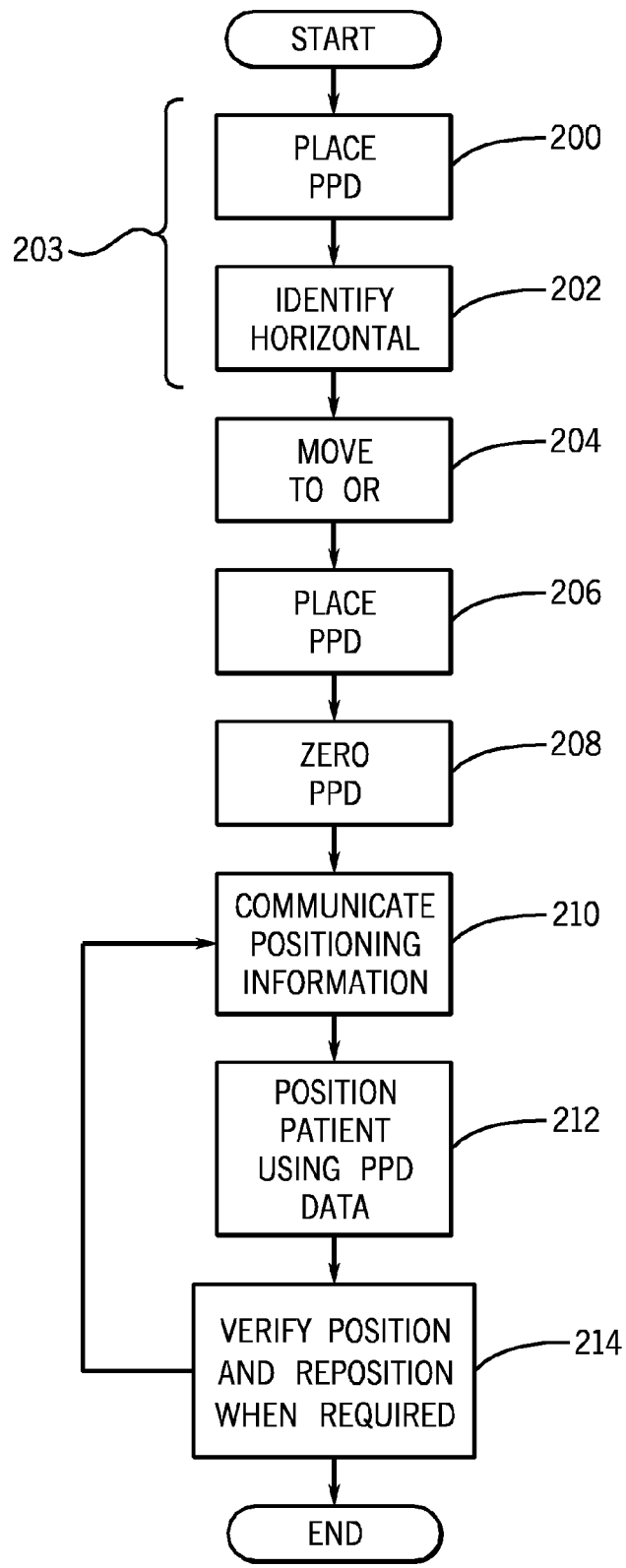
FIG. 12 is a flow chart showing a method of use of the patient positioning device in accordance with the present embodiments.

Referring particularly to FIG. 12, the first step is to place the PPD 100 on the patient, as indicated at process block 200. When a patient is pre-admitted to the hospital, the horizontal reference 132 is identified (at process block 202), such as using a brace 130 and the PPD 100 positioned on the PSIS points, as described above. The PSIS line is typically determined when the patient is standing, and the PSIS points are typically marked with visible markers. If there is any anatomical deficiencies, such as pelvic obliquity or leg-length discrepancy, for example, blocks are typically used to bring the PSIS line to be collinear with the horizontal. The blocks may also be used when any braces or any other anatomical landmarks are used to identify the horizontal line 132 when the patient is standing. The PPD 100 can then be "zeroed" to the corrected condition, as defined by an experienced surgeon, and thus the PPD 100 can be used to assist in correcting leg-length deficiencies and other abnormalities.

After the pre-op procedures 203 are complete, the patient is moved to the operating room and placed in the lateral decubitus position, as indicated at process block 204. A PPD 100 may be again positioned relative to the line previously defined by the PSIS points and/or horizontal line 132. Optionally, at process block 208, the PPD 100 may be zeroed or recalibrated to determine a new horizontal line 132 due to the patient moving from an intake location to the operating room. The PPD 100 wirelessly communicates positioning information to a processor unit 110 (e.g., a laptop) or a display 112 (or receiver 114), as indicated at process block 210. Using the positioning information provided by the PPD 100, the surgeon then positions the patient to ensure that the patient starts the surgery with the PSIS line vertical, as indicated at process block 212, or in a position suitable for correction of the abnormalities discussed above.

Figure 13:
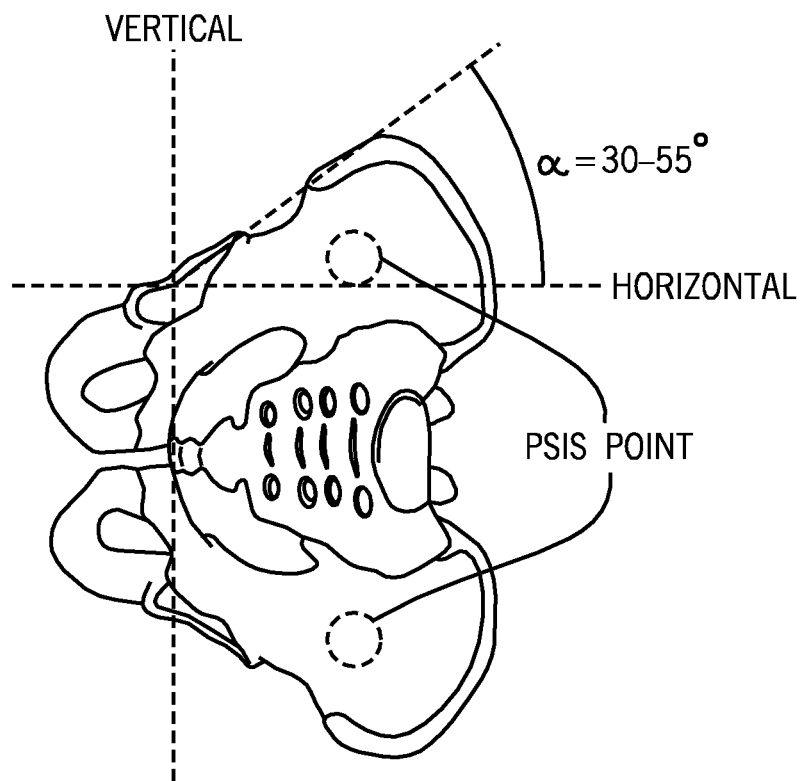
FIG. 13 is an anatomical view of the pelvis with the vertical and horizontal lines identified with the patient in the lateral position.

It is assumed that the patient is lying on their side, with approximately the PPD 100 z-axis pointing up (in line with their pelvis and the gravitational axis), the y-axis pointing towards their feet and the x-axis pointing out of the body. During the THR procedure, the surgeon will assume that there is no pelvic rotation when the patient is in the lateral position. However, it has been found that there is generally considerable coronal tilt and roll, which has been shown to correlate with increased probabilities for undesirable outcomes. Typically, the surgeon will also assume that the alpha angle is between 30 to about 55 degrees (see FIG. 13), and will use conventional alignment instruments to find the optimum prosthetic acetabular cup position before implanting the cup. At process block 214, the systems and methods described herein allow verification and repositioning of the patient and/or the implant prior to using conventional mechanical alignment guides. The systems and methods also allow referencing the acetabular orifice to the mechanical alignment guides. These systems and methods are beneficial in that they minimize error in final implant position.

In an exemplary THR procedure described below, the PPD 100 is mounted directly to the patient. As discussed above, a variety of suitable reference points and mounting options are available. Given the small size of the PPD 100, an additional mounting option is that of an adhesive patch 160 applied directly to the skin commonly used in surgery (see FIGS. 2 and 7). In this example, during pre-surgery preparation, the frame 140 may be used to provide a reference plane positioned relative to the ASIS points (see FIG. 6) as the patient is standing. The PPD 100 is mounted directly to the skin relative to the frame 140 and adhered to the patient, then the frame may be removed. The area directly over the sacrum and between the two iliums of the pelvis is usually relatively clear of fatty deposits even in the heaviest patients, and the fascia are close to the surface. Thus, this is a good location for the PPD 100.

In one embodiment, a single PPD 100 may be used during a THR procedure. The PPD 100 is used to record the horizontal reference using ASIS points as described above, or the left and right PSISs may also be used collinear with the line that intersects the ASIS points or PSIS line. The patient is then repositioned to ensure that the reference horizontal is now the vertical while the patient is in the lateral decubitus position. The surgeon may now use conventional mechanical alignment tools to implant the prosthetic acetabular cup.

In another embodiment, two PPDs 100 may be used during a THR procedure. One of the PPDs is used to identify the ASIS points or PSIS line when the patient is standing, as described above. Then the patient is positioned in the lateral decubitus position on the operating room table. The first PPD 100 may be used for tracking a vector that defines the orientation of the PSIS line. The surgeon may operate to remove some or all of the osteophytes so a plane defined by the orifice of the acetabulum can be identified. The second PPD 100 may be used to reference the plane of the orifice of the acetabulum. The surgeon may now implant the prosthetic acetabular cup using conventional mechanical alignment tools with the cup introducer normal to the orifice of the acetabulum. It is often the case that the surgeon routinely removes osteophytes and other growths to present a clean acetabular cup rim reference plane for implantation. In this situation, the secondary PPD 100 referenced against the first PPD 100 may be used to verify the creation of the reference plane by being placed temporarily on the prepared cup rim. Thus, the surgeon can use this information to verify that the surgical site has been prepared correctly before reaming begins.

In alternative embodiments, the PPD 100 can be configured to provide the orientation of a distinctive axis of the patient relative to the vertical. In addition to providing orientation of the patient, a second PPD 100 may also be used to provide the orientation of a distinctive axis of a surgical tool relative to the vertical. In some embodiments, this may be achieved by having a PPD 100 on the cup introducer. The PPD 100 may be removable so that when the surgeon is impacting the cup introducer, the PPD 100 is not attached to the cup introducer. In other embodiments, the PPD 100 may remain attached to the cup introducer.

Figure 14:
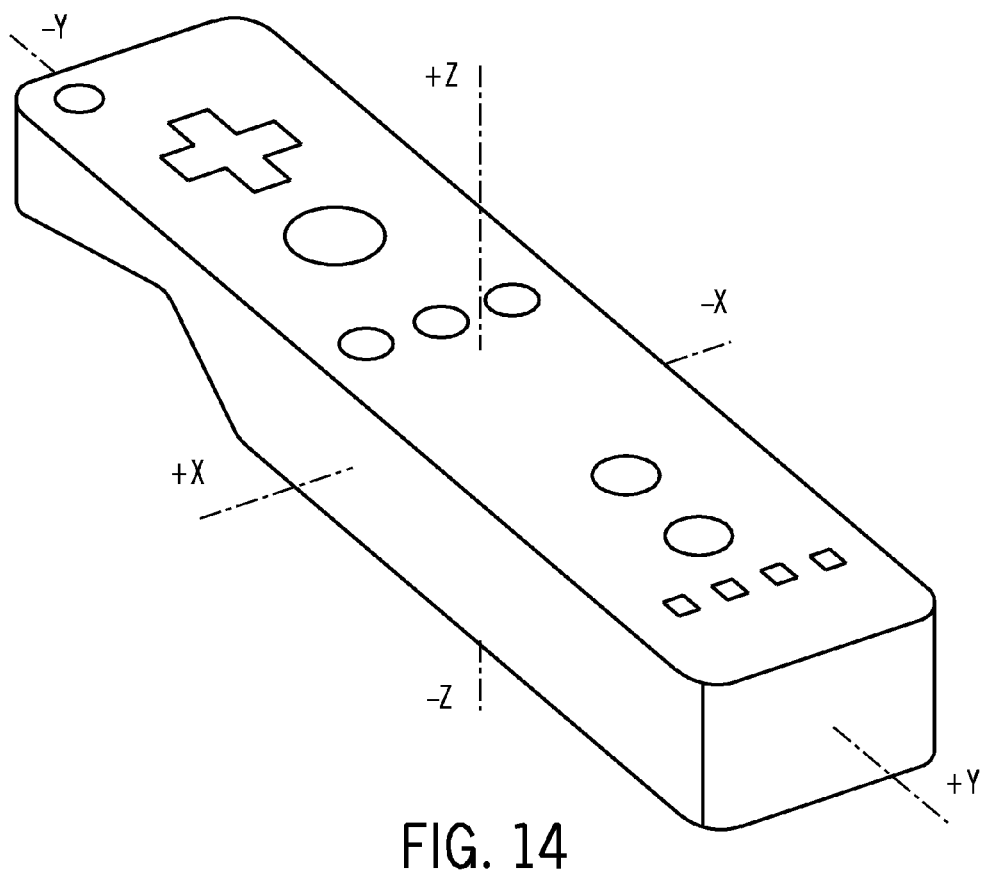
FIG. 14 is a view showing the axes of a Wii Remote used in experimental implementations of a patient positioning device.

In one implementation example of a PPD 100, a 3-axis accelerometer with Bluetooth communication was implemented to track the position of the PSIS during standing and after orientation by an experienced surgeon. The system implemented was made using commercially available hardware, the so-called "Wiimote" provided as part of the Nintendo Wii gaming system. The PPD 100 was comprised of an Analog Devices 3-axis accelerometer (ADXL330) and communicates via proprietary code using a Broadcom Bluetooth IC (BCM2042). Software was generated to allow monitoring of the orientation of the Wiimote control. For the purposes used here, the axes of the Wiimote are defined as shown in FIG. 14.

The procedure used was as follows:

1. A volunteer had the Wiimote attached to a belt with the buttons facing the patient's back and the positive x-axis down and adhered in place level with the PSIS line.

2. The volunteer was told to stand in a relaxed position and the signals from the Wiimote were recorded. In this position, the x-axis approximately aligned with the vertical axis and the y/z plane was parallel to the floor. If the x-axis was entirely aligned with gravity, the Wiimote read 1 (a full signal), and any deviation from gravity allowed the angle to be calculated. This measured angle in the x-axis was stored as a reference angle A.

3. The volunteer then laid down on their side on an exam table and was positioned by an experienced surgeon as if being prepared for surgery.

4. At this point, the y-axis of the sensor was oriented vertically. By subtracting the reference angle A from the y-axis reading, a "true" angular orientation, relative to the relaxed standing orientation was obtained.

5. The patient then got off the table and stood, and the process in steps 2-4 was repeated five times on each side.

By zeroing the signal in this manner, any influences in the relaxed hip positions was neglected. The tilt of the pelvis was usually approximately three degrees off the vertical when the surgeon was aiming for a vertical orientation. Patients with large tilts appeared to show this effect on both sides. Likewise significant errors in the roll alignment were also observed, suggesting that even in the hands of an experienced surgeon, and with easily handled patients, it is difficult to achieve ideal orientation without the aid of a positioning device.

In another implementation example, the calculation of orientation of axes in a three-axis remote using signals from one or more axis was shown.

Figure 15:
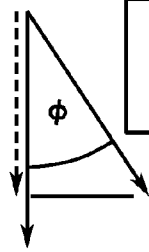
FIG. 15 is a view showing a calculation of orientation using one axis.

To calibrate orientation using one axis, the accelerometer must be zeroed by placing parallel, anti-parallel and perpendicular to the gravity direction (see FIG. 15). Once the values returned for these directions have been obtained, a calibration curve can be generated such that x=+/−1 is the value reported when the sensor is parallel and anti-parallel.

With regard to orientation using multiple axes, at any particular time, the sensors on a three-axis accelerometer measure their specific values relative to gravity. If an axis is perpendicular to gravity, its reported value is zero. Thus each axis yields an orientation of the sensor in one direction relative to gravity. It is noted however, that this orientation is rotation invariant around the gravity direction and can therefore not be used to determine rotation of the sensor around the gravitational axis. However, rotation of the sensor around one if its primary axes can be readily determined, so long as that axis is not in line with gravity.

Figure 16:
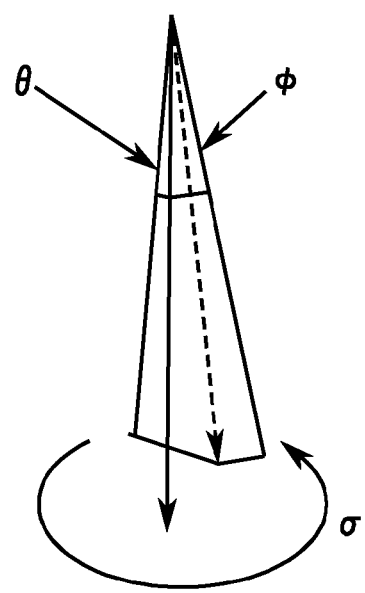
FIG. 16 is a view showing a schematic layout of the position of a patient positioning device in accordance with the present embodiments.
Figure 17:
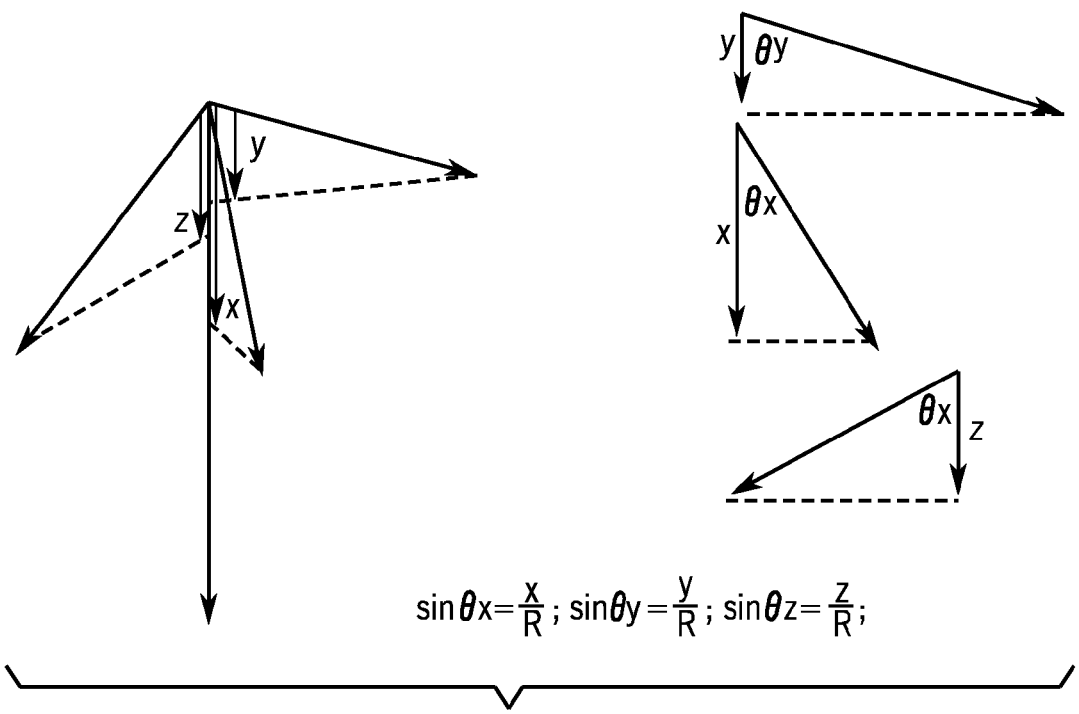
FIG. 17 is a view showing the calculation of a component in the gravitational direction for each of the three axes.

Many commercially available electronic packages include other sensors to enhance the detection process. For example, GPS units frequently include gyroscopic sensors that can detect rotation around a specified axis. The Wiimote enhancement known as the "Wii MotionPlus" also available under the trademark from Nintendo of America adds gyroscopic detection to the standard Wii interface. This add-on for the Wiimote uses one dual-axis gyroscope (variously reported to be the InvenSense IDG-500 or 650) and a single axis gyroscope (Epson TOYOCOM X3500W). Thus, this device allows six degrees of freedom detection (all three translation axes and all three rotational axes) and therefore can track absolute orientation at all times. An alternative piece of hardware available from Sparkfun Electronics is the WiTilt V3 that utilizes a Freescale MMA7261QT 3-axis accelerometer, and a Melexis MLX90609-E2 gyroscope. By simple geometry, the 3-axis signal can be mapped to an orientation relative to gravity, and the gyroscope signal can be used to measure rotational acceleration around an axis. Thus the three coupled axes in FIG. 16 can be simplified by:

$$\theta = \tan^{-1}\left(\frac{y}{\sqrt{x^2 - z^2}}\right), \varphi = \tan^{-1}\left(\frac{x}{\sqrt{y^2 - z^2}}\right);$$

where θ=angle of the x-axis with the vertical and φ=angle of the y-axis with the vertical. Therefore if the starting position is known, the absolute orientation of the detector can be determined through monitoring these outputs and integrating the acceleration in each of the axes/planes.

A drawback with the WiTilt is that the gyroscope sensor is 150 degrees per second, whereas the InvenSense gyroscope has a range of between 500 and 2,000 degrees per second, yielding a much better tolerance to rapid position changes.

With a full six degree of freedom (6DOF) sensor, accelerations in all three direction axes are available, along with orientation around each of those axes. Therefore the direction axes give orientation relative to gravity and translational acceleration, and the rotational sensors yield rotational acceleration. By integrating each of these signals twice (once to velocity, and then to position), absolute position and altitude can be determined relative to the starting point.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this invention.

We claim:
1. A method for providing patient position information, the method comprising:
    arranging a patient positioning device on a patient in a predefined location using a mounting element, wherein the patient positioning device is configured to determine a relative position of the patient positioning device with respect to at least one known axis of the patient;
    establishing, using a processor, at least one axis of reference external to the patient positioning device and the at least one known axis;
    indicating, using the processor, an orientation of the patient using at least the predefined location, the at least one known axis, and the at least one axis of reference external to the patient positioning device;
    indicating, using the processor, updated orientations of the patient over time using at least the predefined location, the at least one known axis, and the at least one axis of reference external to the patient positioning device without the use of further physical references communicating to the patient positioning device its relation to the physical reference,
    wherein arranging includes placing a first patient positioning device on the patient during a pre-operative preparation and identifying a horizontal reference.
2. The method according to claim 1: further including calibrating, using the processor, the patient positioning device to map an x-axis, a y-axis, and a z-axis to an orientation relative to gravity.
3. The method according to claim 2: further including measuring rotational acceleration around at least one of the x-axis, the y-axis, and the z-axis using an accelerometer.
4. The method according to claim 1:
    wherein arranging the patient positioning device comprises orienting the patient positioning device so the at least one known reference axis of the patient positioning device aligns with at least one known axis of the patient.
5. The method according to claim 4:
    wherein orienting the patient positioning device includes orienting a brace relative to a pelvic reference, and orienting the patient positioning device relative to the brace.
6. The method according to claim 5:
    wherein orienting determines a horizontal axis of the pelvic reference.
7. The method according to claim 1:
    wherein indicating a position of the patient and indicating updated positions of the patient comprises wirelessly communicating patient position information to a display system configured to display the patient position information.
8. The method according to claim 1:
    wherein arranging includes placing the patient positioning device on the patient while the patient is standing.

9. The method according to claim 1:
wherein arranging includes placing the patient positioning device on the patient while the patient is in a lateral position.

10. The method according to claim 1:
wherein arranging includes placing the patient positioning device on the low back of the patient.

11. The method according to claim 1:
wherein arranging includes removably securing the patient positioning device to the patient using an adhesive patch.

12. The method according to claim 1: further including monitoring, using the processor, the updated positions of the patient over time and positioning at least one of (i) the patient and (ii) a surgical tool based on the updated positions of the patient over time.

13. The method according to claim 1: further including tracking, using the processor, a position of the patient with respect to a first axis, a second axis transverse to the first axis, and a third axis transverse and an absolute reference including at least one of gravity and a magnetic pole and a radio direction.

14. A method for positioning at least one of (i) a patient and (ii) a surgical tool during an orthopedic procedure, the method comprising:
arranging a patient positioning device on a patient in a predefined location using a mounting element;
calibrating, using a processor, the patient positioning device to determine at least a horizontal reference of a pelvis of the patient while the patient is standing;
placing the patient in a lateral position;
relating, using the processor, the horizontal reference of the pelvis to a gravitational reference with the patient in the lateral position;
communicating, using the processor, patient position information from the patient positioning device, the patient position information including an angular displacement between the horizontal reference of the pelvis and the gravitational reference;
indicating, using the processor, an orientation of the pelvis based on the communicated patient position information; and
positioning at least one of the pelvis and the surgical tool based on the indicated patient position information.

15. The method according to claim 14: calibrating the patient positioning device includes mapping, using the processor, an x-axis, a y-axis, and a z-axis to an orientation relative to gravity.

16. The method according to claim 15: further including measuring rotational acceleration around at least one of the x-axis, the y-axis, and the z-axis using an accelerometer.

17. The method according to claim 14:
wherein communicating comprises wirelessly communicating patient position information to a display system and indicating includes displaying a visual indicator of the orientation of the pelvis.

* * * * *